(12) United States Patent
Vandeputte et al.

(10) Patent No.: US 11,739,034 B2
(45) Date of Patent: Aug. 29, 2023

(54) RECOVERY OF ISOPRENE AND CPD FROM A PYGAS STREAM

(71) Applicant: SABIC GLOBAL TECHNOLOGIES B.V., Bergen op Zoom (NL)

(72) Inventors: Aäron Gabriël Rogier Vandeputte, Sittard (NL); Mamilla Sekhar Babu, Sittard (NL)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 17/635,452

(22) PCT Filed: Aug. 12, 2020

(86) PCT No.: PCT/IB2020/057576
§ 371 (c)(1),
(2) Date: Feb. 15, 2022

(87) PCT Pub. No.: WO2021/048657
PCT Pub. Date: Mar. 18, 2021

(65) Prior Publication Data
US 2022/0306552 A1    Sep. 29, 2022

Related U.S. Application Data

(60) Provisional application No. 62/898,981, filed on Sep. 11, 2019.

(51) Int. Cl.
C07C 6/04 (2006.01)
C07C 7/04 (2006.01)

(52) U.S. Cl.
CPC . *C07C 6/04* (2013.01); *C07C 7/04* (2013.01)

(58) Field of Classification Search
CPC ............... C07C 6/04; C07C 7/04; C07C 2/50
See application file for complete search history.

(56) References Cited

U.S. PATENT DOCUMENTS

| 2,733,279 A | 1/1956 | Wilson et al. |
| 6,958,426 B2 | 10/2005 | Tian et al. |

(Continued)

FOREIGN PATENT DOCUMENTS

| WO | WO 2017/103736 | 6/2017 |
| WO | WO 2017/168320 | 10/2017 |

OTHER PUBLICATIONS

Cheung, T. T. Peter, "Cyclpentadiene and Dicyclopentadiene," Petroleum Technology, vol. 1-2, Part III, Kir-Othmer Encyclopedia of Chemical Technology, (Ed.)., 2001.

(Continued)

*Primary Examiner* — Thuan D Dang
(74) *Attorney, Agent, or Firm* — Norton Rose Fulbright US LLP

(57) ABSTRACT

Systems and methods for recovering cyclopentadiene and/or isoprene from a mixture comprising $C_5$ hydrocarbons are disclosed. A $C_5$ mixture comprising cyclopentadiene and/or isoprene is flowed into a dimerization unit to form dimers. The dimers are then separated from the unreacted $C_5$ hydrocarbons. The separated dimers are monomerized to form a stream comprising cyclopentadiene and/or isoprene, which is subsequently separated to form a first product stream comprising primarily isoprene and a second product stream comprising primarily cyclopentadiene.

20 Claims, 3 Drawing Sheets

(56) References Cited

U.S. PATENT DOCUMENTS

| | | |
|---|---|---|
| 7,041,862 B2 | 5/2006 | Powers |
| 10,047,022 B2 | 8/2018 | Ramanujam et al. |
| 10,065,907 B2 | 9/2018 | Abdelghani |

OTHER PUBLICATIONS

Hsu et al., "Simplification and Intensification of a C5 Separation Process" *Ind. Eng. Chem. Res.* 2015, 54(40), pp. 9798-9804.

International Search Report and Written Opinion issued in Corresponding PCT Application No. PCT/IB2020/057576, dated Nov. 9, 2020.

Szekeres et al., *Thermal Dimerization Of Cyclopentadiene And Its Reaction With Isoprene.* 1976. Department of Chemical Technology, Technical University Budapest.

Wang, Y. "Optimization of C5 separation and production process." 2014 International Conference on Economic Management and Social Science (EMSS 2014), Department of automatic control, Nanjing College of Chemical Technology, Nanjing, 210048, China.

RECOVERY OF ISOPRENE AND CPD FROM A PYGAS STREAM

CROSS REFERENCE TO RELATED APPLICATIONS

This application is a national phase application under 35 U.S.C. § 371 of International Application No. PCT/IB2020/057576, filed Aug. 12, 2020, which claims the benefit of priority of U.S. Provisional Patent Application No. 62/898,981 filed Sep. 11, 2019, the contents of which applications are hereby incorporated by reference in their entirety.

FIELD OF INVENTION

The present invention generally relates to production of isoprene and cyclopentadiene (CPD). More specifically, the present invention relates to systems and methods for recovering cyclopentadiene and/or isoprene from a mixture that contains $C_5$ hydrocarbons.

BACKGROUND OF THE INVENTION

Cyclopentadiene (CPD) is used as a highly reactive intermediate for producing resins such as unsaturated polyesters and aromatic hydrocarbons. Isoprene ($CH_2$=C($CH_3$)—CH=$CH_2$) is an important petrochemical. It is used, for example, in the production of rubbers and plastics. Conventionally, both cyclopentadiene and isoprene can be produced as byproducts of hydrocarbon steam cracking to produce light olefins. In general, the cyclopentadiene and isoprene from the steam cracking process are present in pyrolysis gas (pygas) along with various other hydrocarbons. Thus, separation and/or purification processes are needed to produce purified cyclopentadiene and isoprene.

Currently, both cyclopentadiene and isoprene are separated from $C_5$ fractions of pygas using a system comprising a combination of reactors and extractive distillation columns. More specifically, a $C_5$ stream is processed under conditions to dimerize the cyclopentadiene to form dicyclopentadiene (DiCPD). The reaction mixture is then separated to remove $C_5$ hydrocarbons, which have lower boiling points than DiCPD. The higher boiling point mixture including DiCPD is then flowed to a distillation column to separate DiCPD as a bottom product. The overhead stream from the distillation column is then processed in an extractive distillation unit configured to recover isoprene. However, the current method demands high capital expenditures and operational costs for building and operating the combinations of reactors, distillation column, and extractive distillation columns. Additionally, the recovery rates for cyclopentadiene and isoprene using the conventional method are relatively limited, which contributes to the high production costs for CPD and isoprene.

Overall, while the systems and methods for recovering cyclopentadiene and isoprene from $C_5$ hydrocarbon mixtures exist, the need for improvements in this field persists in light of at least the aforementioned drawback of the conventional systems and methods.

BRIEF SUMMARY OF THE INVENTION

A solution to at least some of the above-mentioned problems associated with the systems and methods for recovering cyclopentadiene and/or isoprene from a $C_5$ hydrocarbon mixture has been discovered. The solution resides in contacting the $C_5$ hydrocarbon mixture with a dienophile in a dimerization unit to produce DiCPD and isoprene-cyclopentadiene codimers, then monomerizing the DiCPD and isoprene-cyclopentadiene codimers in a monomerization unit to produce CPD and isoprene. This can be beneficial for at least eliminating the requirement for extractive distillation columns in the system, thereby reducing operational costs and capital expenditure for producing CPD and isoprene. Furthermore, this method can include using a series of dimerization reactors with a dienophile added intermittently to increase the conversion rate of the CPD and isoprene into dimers, thereby increasing overall CPD and isoprene recovery rate from $C_5$ hydrocarbon mixtures compared to the conventional methods. Therefore, the method of the present invention provides a technical solution to at least some of the problems associated with the conventional systems and methods for recovering CPD and isoprene mentioned above.

Embodiments of the invention include a method of obtaining isoprene and/or cyclopentadiene from a $C_5$ stream comprising primarily $C_5$ hydrocarbons. The method comprises contacting a feed stream comprising primarily $C_5$ hydrocarbons with a dienophile under reaction conditions sufficient to dimerize cyclopentadiene and isoprene present in the feed stream to produce a first intermediate stream comprising dicyclopentadiene, cyclopentadiene isoprene, unreacted $C_5$ hydrocarbons, and isoprene. The method comprises processing the first intermediate stream to produce a first product stream comprising primarily isoprene and a second product stream comprising primarily cyclopentadiene.

Embodiments of the invention include a method of obtaining isoprene and/or cyclopentadiene from a $C_5$ stream comprising primarily $C_5$ hydrocarbons. The method comprises contacting a feed stream comprising primarily $C_5$ hydrocarbons with a dienophile under reaction conditions sufficient to dimerize cyclopentadiene and isoprene present in the feed stream to produce a first intermediate stream comprising dicyclopentadiene, cyclopentadiene isoprene, unreacted $C_5$ hydrocarbons, and isoprene. The method comprises separating the first intermediate stream into (1) a second intermediate stream comprising primarily the unreacted $C_5$ hydrocarbons and (2) a third intermediate stream comprising primarily dicyclopentadiene. The method comprises subjecting the third intermediate stream to conditions sufficient to monomerize dicyclopentadiene in the third intermediate stream and to monomerize cyclopentadiene isoprene in the third intermediate stream to produce a fourth intermediate stream comprising isoprene and cyclopentadiene. The method comprises separating the fourth intermediate stream to produce a first product stream comprising isoprene and a second product stream comprising cyclopentadiene.

Embodiments of the invention include a method of obtaining isoprene and/or cyclopentadiene from a $C_5$ stream comprising primarily $C_5$ hydrocarbons. The method comprises separating pygas to produce (1) a feed stream comprising primarily $C_5$ hydrocarbons and (2) and a heavy stream comprising primarily $C_{6+}$ hydrocarbons. The method comprises contacting the feed stream comprising primarily $C_5$ hydrocarbons with a dienophile under reaction conditions sufficient to dimerize cyclopentadiene and isoprene present in the feed stream to produce a first intermediate stream comprising dicyclopentadiene, cyclopentadiene isoprene (codimer), unreacted $C_5$ hydrocarbons, and isoprene. The method comprises separating the first intermediate stream into (1) a second intermediate stream comprising primarily the unreacted $C_5$ hydrocarbons and (2) a third intermediate stream comprising primarily dicyclopentadiene. The method further comprises separating the heavy stream in a distillation column to form a $C_{10}$ stream comprising dicyclopentadiene, a $C_6$ to $C_9$ stream comprising primarily $C_6$ to $C_9$ hydrocarbons, collectively, and a heavy residue stream comprising $C_{10}+$ hydrocarbons. The method further comprises combining the $C_{10}$ stream with the third intermediate stream to form a monomerization unit feed stream and flowing the monomerization unit feed stream into the monomerization unit. The method comprises subjecting the monomerization unit feed stream to conditions sufficient to monomerize dicyclopentadiene in the monomerization unit feed stream and to monomerize cyclopentadiene isoprene in the monomerization unit feed stream to produce a fourth intermediate stream comprising isoprene and cyclopentadiene and residue stream comprising $C_6+$ hydrocarbons. The method comprises separating the fourth intermediate stream to produce a first product stream comprising isoprene and a second product stream comprising cyclopentadiene.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refers to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, includes any measurable decrease or complete inhibition to achieve a desired result.

The term "effective," as that term is used in the specification and/or claims, means adequate to accomplish a desired, expected, or intended result.

The term "$C_n+$ hydrocarbon" wherein n is a positive integer, e.g. 1, 2, 3, 4, or 5, as that term is used in the specification and/or claims, means any hydrocarbon having at least n number of carbon atom(s) per molecule.

The term "stoichiometric number of hydrogen to carbon monoxide" or "$S_N$" as that term is used in the specification and/or claims, refers to a ratio of $[(H_2-CO_2)/(CO+CO_2)]$, where $(H_2-CO_2)$ is the molar concentration difference between hydrogen and carbon dioxide in a mixture or a stream, and $(CO+CO_2)$ is the molar concentration sum between carbon monoxide and carbon dioxide in a mixture or a stream.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

The term "primarily," as that term is used in the specification and/or claims, means greater than any of 50 wt. %, 50 mol. %, and 50 vol. %. For example, "primarily" may include 50.1 wt. % to 100 wt. % and all values and ranges there between, 50.1 mol. % to 100 mol. % and all values and ranges there between, or 50.1 vol. % to 100 vol. % and all values and ranges there between.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which:

FIG. 1A shows a schematic diagram of a system for recovering cyclopentadiene that does not require a dienophile recovery unit; FIG. 1B shows a schematic diagram of a system for recovering cyclopentadiene including a dienophile recovery unit.

DETAILED DESCRIPTION OF THE INVENTION

Figure 1A:
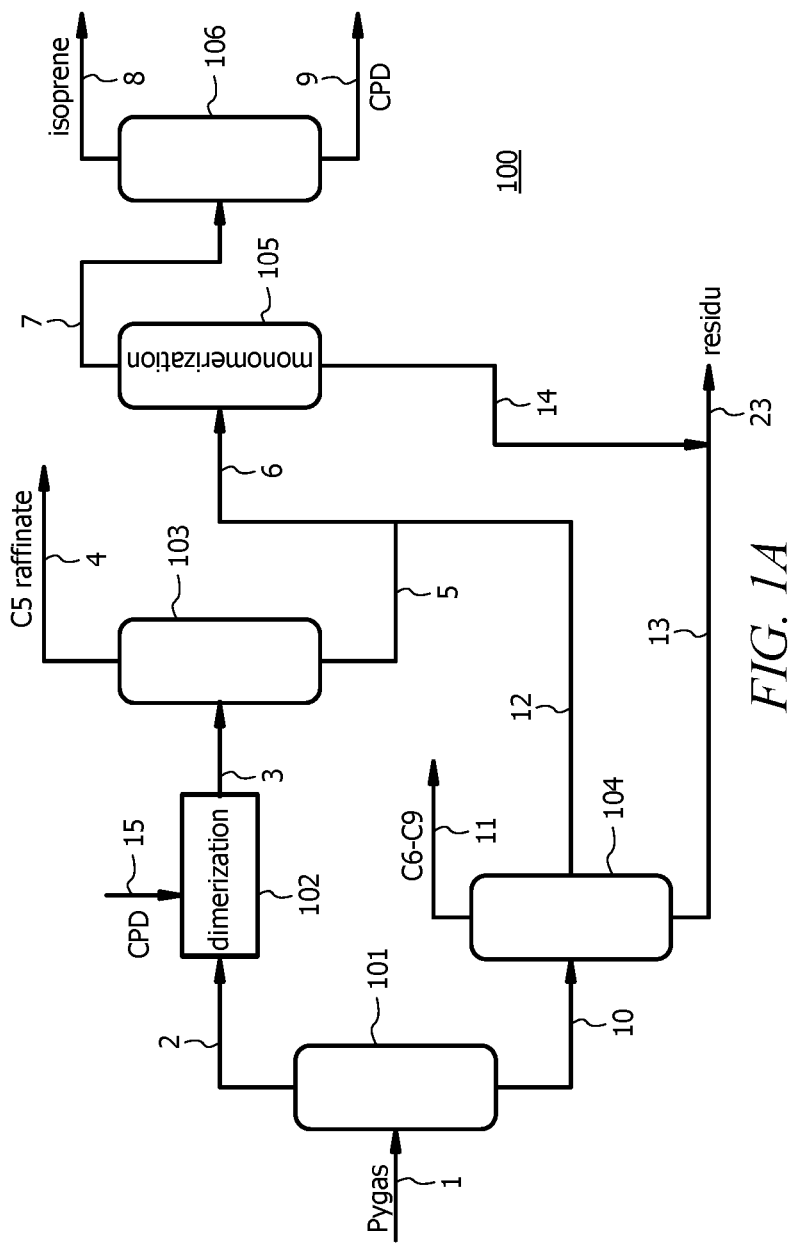
FIGS. 1A and 1B show schematic diagrams of systems for recovering cyclopentadiene and isoprene, according to embodiments of the invention.

A method and a system have been discovered for recovering cyclopentadiene and/or isoprene from a $C_5$ hydrocarbon mixture that includes dimerizing the cyclopentadiene and the isoprene to produce dimers, separating the non-dimers from the produced dimers, and monomerizing the dimers to produce a stream comprising primarily cyclopentadiene and isoprene. Notably, a dienophile can be added into the dimerizing step intermittently to increase the conversion rate of cyclopentadiene and isoprene into dimers, thereby increasing the overall cyclopentadiene and isoprene recovery rate from the $C_5$ hydrocarbon mixture. Additionally, the system does not require an extractive distillation unit, resulting in reduced capital expenditure and operating costs compared to conventional systems and methods. These and other non-limiting aspects of the present invention are discussed in further detail in the following sections.

A. System for Recovering Cyclopentadiene and/or Isoprene

In embodiments of the invention, the system of recovering cyclopentadiene and/or isoprene includes a dimerization unit, a monomerization unit, and two or more separation units. With references to FIGS. 1A and 1B, schematic diagrams are shown of systems 100 and 200, respectively, for recovering cyclopentadiene and/or isoprene.

According to embodiments of the invention, system 100 comprises first separation unit 101 configured to separate pygas stream 1 to form feed stream 2 comprising primarily $C_5$ hydrocarbons and heavy stream 10 comprising hydrocarbons having a boiling point higher than 60° C. ($C_6$+). In embodiments of the invention, first separation unit 101 includes a distillation column. Pygas stream 1 may be obtained from a steam cracking unit. In embodiments of the invention, the $C_5$ hydrocarbons in feed stream 2 include n-pentane, 1-pentene, 2-pentene, 1,3-pentadiene, 1,4-pentadiene, isopentane, cyclopentane, cyclopentene, cylopentadiene, isoprene, or combinations thereof. In embodiments of the invention, feed stream 2 further includes trace amount of $C_4$ and/or $C_6$ hydrocarbons.

According to embodiments of the invention, an outlet of first separation unit 101 may be in fluid communication with an inlet of dimerization unit 102 such that feed stream 2 flows from first separation unit 101 to dimerization unit 102. In embodiments of the invention, dimerization unit 102 is configured to react cyclopentadiene and/or isoprene with a dienophile under reaction conditions to produce first intermediate stream 3 comprising one or more dimers. In embodiments of the invention, dimerization unit 102 includes a series of reactors for achieving high conversion rate of cyclopentadiene and/or isoprene to dimers. The series reactors may include adiabatic boiling point or jacket cooled reactors, operated as plug flow fixed bed or continuously stirred tank reactor, or combinations thereof. Non-limiting examples of the dienophile may include dienes, anhydrides, acrylates, azocompounds, cyanocompounds, and combinations thereof. The dimers may include homodimers, and/or heterodimers. Non-limiting examples of the dimers include dicyclopentadiene, diisoprene, 5-methyl-exo-5-vinyl-norbornene (exo and endo isomers), 5-isopropenyl-2-norbornene (exo and endo isomers), cyclopentadiene quinone (1:1 adduct), or combinations thereof. In embodiments of the invention, first intermediate stream 3 further comprises unreacted $C_5$ hydrocarbons.

In embodiments of the invention, an outlet of dimerization unit 102 is in fluid communication with an inlet of second separation unit 103. According to embodiments of the invention, second separation unit 103 is configured to separate first intermediate stream 3 to form (i) second intermediate stream 4 comprising primarily unreacted $C_5$ hydrocarbons and (ii) third intermediate stream 5 comprising the dimers.

According to embodiments of the invention, an outlet of first separation unit 101 is in fluid communication with third separation unit 104 such that heavy stream 10 flows from first separation unit into third separation unit 104. In embodiments of the invention, third separation unit 104 is configured to separate heavy stream 10 to form $C_6$ to $C_9$ stream 11 comprising primarily $C_6$ to $C_9$ hydrocarbons, $C_{10}$ stream 12 comprising primarily dicyclopentadiene, and heavy residue stream 13 comprising primarily $C_{10}$+ hydrocarbons. Third separation unit 104 may include a distillation column. According to embodiments of the invention, $C_{10}$ stream 12 is combined with third intermediate stream 5 to form monomerization unit feed stream 6.

According to embodiments of the invention, system 100 comprises monomerization unit 105 configured to receive monomerization unit feed stream 6 and monomerize dicyclopentadiene from $C_{10}$ stream 12 and dimers from third intermediate stream 5 to form fourth intermediate stream 7 comprising primarily cyclopentadiene and/or isoprene, collectively, and residue stream 14 comprising hydrocarbons that have boiling points higher than cyclopentadiene and isoprene. In embodiments of the invention, monomerization unit 105 includes a gas phase reactor, in which the dimers are mixed with a heat transfer agent, typically steam and/or hydrogen, or a boiling tank reactor in which the monomers boil up from a high-boiling solvent. In embodiments of the invention, residue stream 14 and heavy residue stream 13 can be combined to form combined residue stream 23.

According to embodiments of the invention, an outlet of monomerization unit 105 is in fluid communication with fourth separation unit 106 such that fourth intermediate stream 7 flows from monomerization unit 105 to fourth separation unit 106. In embodiments of the invention, fourth separation unit 106 is configured to separate fourth intermediate stream 7 to form first product stream 8 comprising primarily isoprene and second product stream 9 comprising primarily cyclopentadiene. Fourth separation unit 106 may include a distillation column.

Figure 1B:
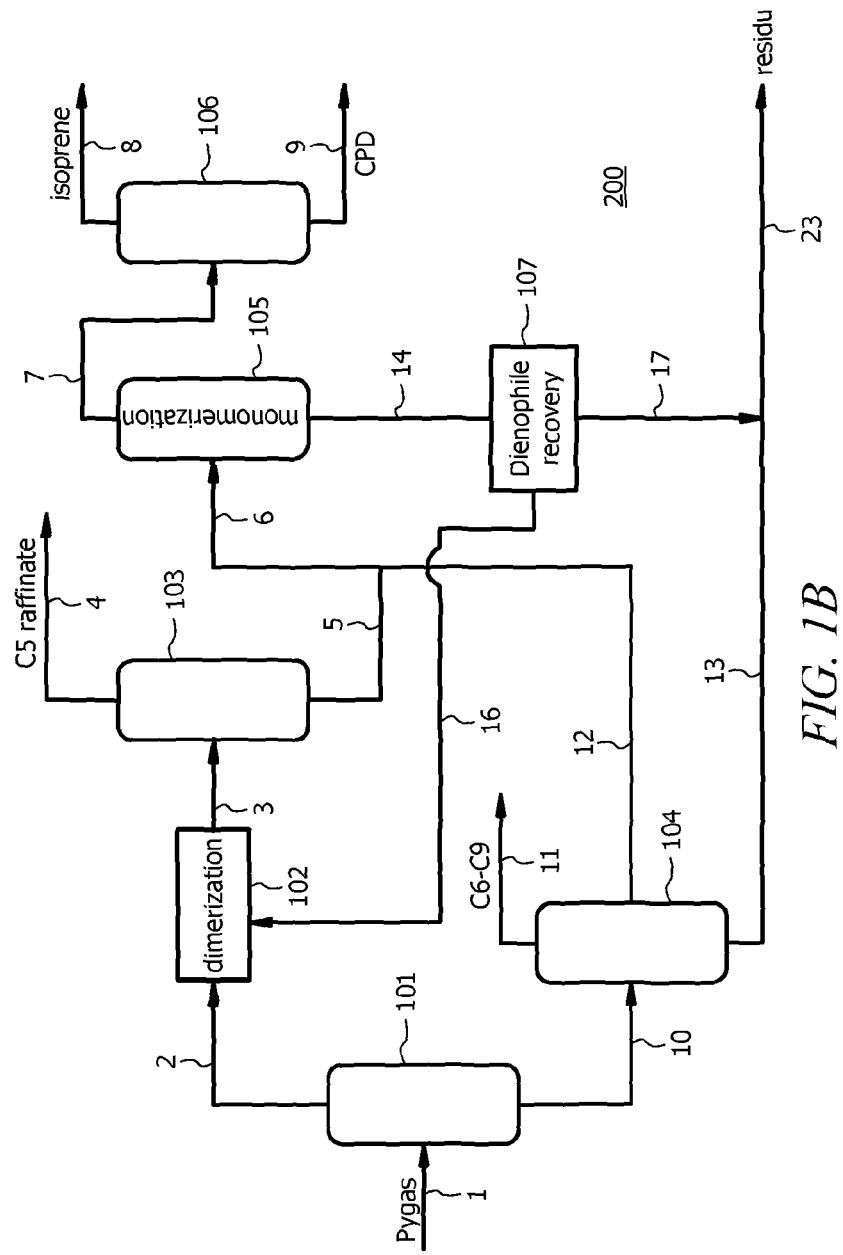

Referring to FIG. 1B, system 200 may include all the units and streams of system 100 as shown in FIG. 1A. According to embodiments of the invention, system 200 further comprises dienophile recovery unit 107. An inlet of dienophile recovery unit 107 may be in fluid communication with an outlet of monomerization unit 105 such that residue stream 14 flows from monomerization unit 105 to dienophile recovery unit 107. In embodiments of the invention, the dienophile added into dimerization unit 102 may include a compound that is not cyclopentadiene. Dienophile recovery unit 107 is configured to recover the dienophile(s) that is not cylopentadiene from residue stream 14 to produce (i) recycle dienophile stream 16 comprising non-cyclopentadiene dienophile(s) and (ii) residue raffinate stream 17. In system 200, non-limiting examples of the dienophile may include anhydrides (e.g., benzoquinone), acrylates, azocompounds, cyanocompounds, and combinations thereof.

According to embodiments of the invention, recycle dienophile stream 16 is flowed back to dimerization unit 102 to provide dienophile(s) for producing the dimers. In embodiments of the invention, residue raffinate stream 17 is combined with heavy residue stream 13 to form combined residue stream 23.

B. Method of Producing Methanol

Figure 2:
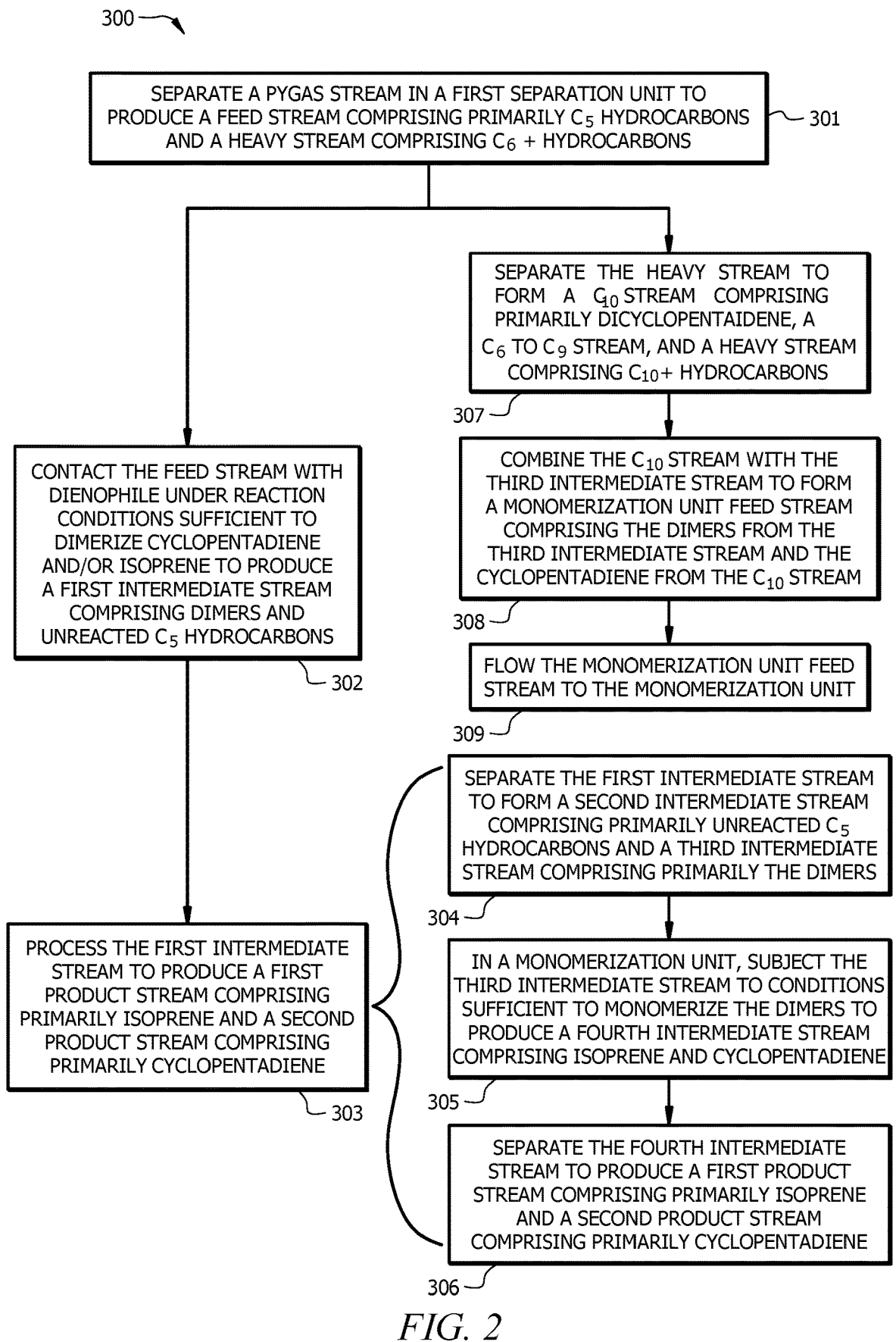
FIG. 2 shows a schematic flowchart for a method of recovering cyclopentadiene and isoprene, according to embodiments of the invention.

Methods of recovering cyclopentadiene and/or isoprene from a $C_5$ hydrocarbon mixture have been discovered. Embodiments of the methods are capable of improving recovery rate of cyclopentadiene and/or isoprene and reduce the operational costs and capital expenditure for recovering cyclopentadiene and/or isoprene compared to conventional methods. As shown in FIG. 2, embodiments of the invention include method 300 for recovering cyclopentadiene and/or isoprene from a mixture comprising $C_5$ hydrocarbons. Method 300 may be implemented by system 100 and/or system 200, as shown in FIG. 1A and FIG. 1B, respectively.

According to embodiments of the invention, as shown in block 301, method 300 includes separating pygas stream 1 in first separation unit 101 to produce (1) feed stream 2 comprising primarily $C_5$ hydrocarbons and (2) heavy stream 10 comprising $C_6$+ hydrocarbons. In embodiments of the invention, pygas stream 1 is obtained from a steam cracking unit for producing light olefins ($C_2$ to $C_4$ olefins). In embodiments of the invention, feed stream 2 comprises cyclopentadiene and/or isoprene. The $C_6$+ hydrocarbons in heavy stream 10 may have boiling points higher than 60° C. In embodiments of the invention, first separation unit 101 comprises a distillation column operated with an overhead boiling range of 30 to 65° C. and a reboiler temperature range of 70 to 110° C. First separation unit 101 may be operated at an operating pressure of 1 to 5 bar and all ranges and values there between including ranges of 1 to 1.5 bar, 1.5 to 2 bar, 2 to 2.5 bar, 2.5 to 3 bar, 3 to 3.5 bar, 3.5 to 4 bar, 4 to 4.5 bar, and 4.5 to 5 bar.

According to embodiments of the invention, as shown in block 302, method 300 includes, in dimerization unit 102, contacting feed stream 2 comprising primarily $C_5$ hydrocarbons with a dienophile under reaction conditions sufficient to dimerize cyclopentadiene and/or isoprene of feed stream 2 to produce first intermediate stream 3 comprising dimers and unreacted $C_5$ hydrocarbons. In embodiments of the invention, non-limiting examples of the dimers include dicyclopentadiene, isoprene cylopentadiene, cyclopentadiene quinone (1:1 adduct), or combinations thereof. At block 302, the dienophile may be added into dimerization unit 102 intermittently via dienophile stream 15. In embodiments of the invention, the reaction conditions at block 302 include a reaction temperature of 50 to 250° C. and all ranges and values there between including ranges of 50 to 60° C., 60 to 70° C., 70 to 80° C., 80 to 90° C., 90 to 100° C., 100 to 110° C., 110 to 120° C., 120 to 130° C., 130 to 140° C., 140 to 150° C., 150 to 160° C., 160 to 170° C., 170 to 180° C., 180 to 190° C., 190 to 200° C., 200 to 210° C., 210 to 220° C., 220 to 230° C., 230 to 240° C., and 240 to 250° C. The reaction conditions at block 302 may include a reaction pressure of 3.5 to 70 bar and all ranges and values there between including ranges of 3.5 to 7 bar, 7 to 14 bar, 14 to 21 bar, 21 to 28 bar, 28 to 35 bar, 35 to 42 bar, 42 to 49 bar, 49 to 56 bar, 56 to 63 bar, and 63 to 70 bar. The reaction conditions at block 302 may include a residence time of 5 to 12000 s and all ranges and values there between including ranges of 5 to 10 s, 10 to 100 s, 100 to 200 s, 200 to 300 s, 300 to 400 s, 400 to 500 s, 500 to 600 s, 600 to 700 s, 700 to 800 s, 800 to 900 s, 900 to 1000 s, 1000 to 2000 s, 2000 to 3000 s, 3000 to 4000 s, 4000 to 5000 s, 5000 to 6000 s, 6000 to 7000 s, 7000 to 8000 s, 8000 to 9000 s, 9000 to 10000 s, 10000 to 11000 s, and 11000 to 12000 s. In embodiments of the invention, at block 302, a conversion rate of cyclopentadiene to dimers is about 90 to 100% and all ranges and values there between including ranges of 90 to 91%, 91 to 92%, 92 to 93%, 93 to 94%, 94 to 95%, 95 to 96%, 96 to 97%, 97 to 98%, 98 to 99%, and 99 to 100%. At block 302, a conversion rate of isoprene to dimers is about 40 to 90% and all ranges and values there between including ranges of 40 to 45%, 45 to 50%, 50 to 55%, 55 to 60%, 60 to 65%, 65 to 70%, 70 to 75%, 75 to 80%, 80 to 85%, and 85 to 90%.

According to embodiments of the invention, as shown in block 303, method 300 includes processing first intermediate stream 3 to produce first product stream 8 comprising primarily isoprene and second product stream 9 comprising primarily cyclopentadiene.

In embodiments of the invention, as shown in block 304, processing step at block 303 comprises, in second separation unit 103, separating first intermediate stream 3 to form (1) second intermediate stream 4 comprising primarily unreacted $C_5$ hydrocarbons and (2) third intermediate stream 5 comprising primarily the dimers. In embodiments of the invention, second separation unit 103 includes a distillation column. Second separation unit 103 may be operated at an overhead range of 35 to 150° C. and a reboiler range of 150 to 250° C. Second separation unit 103 may be operated at an operating pressure of 1 to 7 bar and all ranges and values there between.

In embodiments of the invention, as shown in block 305, processing step at block 303 comprises subjecting, in a monomerization unit 105, third intermediate stream 5 to conditions sufficient to monomerize the dimers in the third intermediate stream 5 to produce fourth intermediate stream 7 comprising isoprene and cyclopentadiene. The subjecting step at block 305 may further produce residue stream 14 comprising unreacted $C_9$ to $C_{11}$ hydrocarbons with a boiling point in the range of 150 to 190° C. In embodiments of the invention, residue stream 14 may comprise one or more dienophiles that are not cyclopentadiene, and residue stream 14 is processed in dienophile recovery unit 107 to produce (i) recycle dienophile stream 16 comprising non-cyclopentadiene dienophile(s) and (ii) residue raffinate stream 17. Recycle dienophile stream 16 may be flowed back to dimerization unit 102. In embodiments of the invention, the conditions sufficient to monomerize the dimers at block 305 include a temperature in monomerization unit 105 in a range of 170 to 400° C. and all ranges and values there between including ranges of 170 to 180° C., 180 to 200° C., 200 to 220° C., 220 to 240° C., 240 to 260° C., 260 to 280° C., 280 to 300° C., 300 to 320° C., 320 to 340° C., 340 to 360° C., 360 to 380° C., and 380 to 400° C. The conditions sufficient to monomerize the dimers at block 305 may include a pressure in monomerization unit 105 in a range of 1 to 5 bar and all ranges and values there between including ranges of 1 to 1.5 bar, 1.5 to 2 bar, 2 to 2.5 bar, 2.5 to 3 bar, 3 to 3.5 bar, 3.5 to 4 bar, 4 to 4.5 bar, and 4.5 to 5 bar. The conditions sufficient to monomerize the dimers at block 305 may include a residence time of monomerization unit 105 in a range of 0.1 to 1000 s and all ranges and values there between including ranges of 0.1 to 1 s, 1 to 10 s, 10 to 100 s, 100 to 200 s, 200 to 300 s, 300 to 400 s, 400 to 500 s, 500 to 600 s, 600 to 700 s, 700 to 800 s, 800 to 900 s, and 900 to 1000 s. In embodiments of the invention, at block 305 about 90 to 99.9% dimers are monomerized.

According to embodiments of the invention, as shown in block 306, processing step at block 303 comprises separating fourth intermediate stream 7 in fourth separation unit 106 to produce first product stream 8 comprising primarily isoprene and second product stream 9 comprising primarily cyclopentadiene. In embodiments of the invention, fourth separation unit 106 includes a distillation column and/or a reactive distillation column. Fourth separation unit 106 may be operated at an overhead boiling range of 30 to 110° C. and a reboiler range of 70 to 130° C. Fourth separation unit 106 may be operated at an operating pressure of 1 to 15 bar and all ranges and values there between including ranges of 1 to 3 bar, 3 to 5 bar, 5 to 7 bar, 7 to 9 bar, 9 to 11 bar, 11 to 13 bar, and 13 to 15 bar. In embodiments of the invention, first product stream 8 comprises more than 98 wt. % isoprene. Second product stream 9 comprises more than 98 wt. % cyclopentadiene.

According to embodiments of the invention, as shown in block 307, method 300 further comprises separating, in third separation unit 104, heavy stream 10 to form $C_{10}$ stream 12 comprising primarily dicyclopentadiene, $C_6$ to $C_9$ stream 11 comprising $C_6$ to $C_9$ hydrocarbons, and heavy residue stream 13 comprising $C_{10}$+ hydrocarbons. In embodiments of the invention, third separation unit 104 comprises a distillation column. $C_{10}$ stream 12 may be a side draw from the distillation column. In embodiments of the invention, third separation unit 104 is operated at an overhead boiling range of 35 to 110° C. and reboiler range of 100 to 300° C. Third separation unit 104 may be operated at an operating pressure of 1 to 5 bar and all ranges and values there between including ranges of 1 to 1.5 bar, 1.5 to 2 bar, 2 to 2.5 bar, 2.5 to 3 bar, 3 to 3.5 bar, 3.5 to 4 bar, 4 to 4.5 bar, and 4.5 to 5 bar.

According to embodiments of the invention, as shown in block 308, method 300 further comprises combining $C_{10}$ stream 12 with third intermediate stream 5 to form monomerization unit feed stream 6 comprising dimers from third intermediate stream 5 and cyclopentadiene from $C_{10}$ stream 12. In embodiments of the invention, as shown in block 309, method 300 further includes flowing monomerization unit feed stream 6 into monomerization unit 105. The $C_{10}$ hydrocarbons and other dimers of monomerization unit feed stream 6 can be monomerized to form cyclopentadiene, isoprene, and/or the dienophile in monomerization unit 105. According to embodiments of the invention, method 300 is capable of recovering at least 99% of cyclopentadiene and at least 50% of the isoprene from pygas stream 1.

Although embodiments of the present invention have been described with reference to blocks of FIG. 2, it should be appreciated that operation of the present invention is not limited to the particular blocks and/or the particular order of the blocks illustrated in FIG. 2. Accordingly, embodiments of the invention may provide functionality as described herein using various blocks in a sequence different than that of FIG. 2.

As part of the disclosure of the present invention, a specific example is included below. The example is for illustrative purpose only and is not intended to limit the invention. Those of ordinary skill in the art will readily recognize parameters that can be changed or modified to yield essentially the same results.

EXAMPLE

Simulations of a Process for Recovering Cyclopentadiene and Isoprene from Pygas

Simulations were performed with ASPEN Plus platform to simulate the process of recovering cyclopentadiene and isoprene from pygas using a system as shown in FIG. 1A. In the simulations, 12.5 ton/hr of pygas was fed into the system. Dimerization was performed in two stages at a temperature of 140° C. The total residence time for the dimerization unit was 2 hours. About 2.5 ton/hr cyclopentadiene was fed between the two stages of dimerization as the dienophile. The results of the simulations depicting the composition and the flow rate of each stream in FIG. 1A were shown in Tables 1 and 2.

TABLE 1

| | 1 | 2 | 3 | 4 | 5 | 6 | 7 | 8 |
|---|---|---|---|---|---|---|---|---|
| Mass flow (t/h) | 12.5 | 5.06 | 7.56 | 3.64 | 3.92 | 5.30 | 5.13 | 0.57 |
| Mass frac | | | | | | | | |
| ΣC4 | 1.5 | 3.7 | 2.5 | 5.1 | | | | |
| C5 20-34° C. | 6.6 | 16.3 | 10.9 | 22.6 | | | | |
| Isoprene | 9.3 | 23 | 7.9 | 16.4 | | | 11.0 | 99.8 |
| C5 33-40° C. | 9.0 | 22.2 | 14.9 | 30.8 | | | | |
| CPD | 7.0 | 17.3 | 0.3 | 0.6 | | | 88.8 | |
| piperylene | 5.0 | 12.4 | 8.1 | 16.8 | | | 0.1 | 0.2 |
| C5 40° C.-50° C. (excl piperylene) | 1.9 | 4.7 | 3.1 | 6.5 | | | | |
| C6 50-60° C. | 0.2 | 0.5 | 0.5 | 1.0 | | | | |
| C6-C7 60-80° C. | 6.5 | | | | | | | |
| Benzene | 34.4 | | | | | | | |
| Fraction 80-160° C. | 5.3 | | | | | | | |
| Fraction 160-180°(excl DCPD) | 1.4 | 14.7 | | | 28.4 | 24.3 | | |
| DCPD | 9.7 | 37 | | | 71.4 | 75.6 | | |
| Fraction >180° C. | 2.2 | 0.1 | | | 0.2 | 0.1 | | |

TABLE 2

| | 9 | 10 | 11 | 12 | 13 | 14 | 15 |
|---|---|---|---|---|---|---|---|
| Mass flow (t/h) | 4.56 | 7.44 | 5.78 | 1.39 | 0.28 | 0.18 | 2.50 |
| Mass frac | | | | | | | |
| ΣC4 | | | | | | | |
| C5 20-34° C. | | | | | | | |
| Isoprene | 0.0 | | | | | | |
| C5 33-40° C. | | | | | | | |
| CPD | 99.8 | | | | | | 100 |
| piperylene | 0.1 | | | | | | |
| C5 40° C.-50° C. (excl piperylene) | | | | | | | |
| C6 50-60° C. | | | | | | | |
| C6-C7 60-80° C. | | 10.9 | 14.1 | | | | |
| Benzene | | 57.8 | 74.5 | | | | |
| Fraction 80-160° C. | | 8.9 | 11.5 | | | | |
| Fraction 160-180°(excl DCPD) | | 2.4 | | 12.6 | | 100 | |
| DCPD | | 16.3 | | 87.4 | | | |
| Fraction >180° C. | | 3.7 | | | 100 | | |

The systems and processes described herein can also include various equipment that is not shown and is known to one of skill in the art of chemical processing. For example, some controllers, piping, computers, valves, pumps, heaters, thermocouples, pressure indicators, mixers, heat exchangers, and the like may not be shown.

In the context of the present invention, at least the following 16 embodiments are described. Embodiment 1 is a method of obtaining isoprene and/or cyclopentadiene from a $C_5$ stream. The method includes contacting, in a dimerization unit, a feed stream containing primarily $C_5$ hydrocarbons with a dienophile under reaction conditions sufficient to dimerize cyclopentadiene and isoprene present in the feed stream to produce a first intermediate stream containing dicyclopentadiene, cyclopentadiene isoprene, and unreacted $C_5$ hydrocarbons. The method further includes processing the first intermediate stream to produce a first product stream containing primarily isoprene and a second product stream containing primarily cyclopentadiene. Embodiment 2 is the method of embodiment 1, wherein the reaction conditions in the contacting step include a reaction temperature of 50 to 250° C. and reaction pressure of 3.5 to 70 bar. Embodiment 3 is the method of either of embodiments 1 or 2, wherein the contacting step is conducted in a dimerization unit including a series of reactors. Embodiment 4 is the method of embodiment 3, wherein, in the contacting step, the dienophile is added to the dimerization unit intermittently. Embodiment 5 is the method of any of embodiments 1 to 4, wherein the dienophile is selected from the group consisting of cyclopentadiene, anhydrides, acrylates, azocompounds, cyanocompounds, and combinations thereof. Embodiment 6 is the method of any of embodiments 1 to 5, further including prior to the contacting step, separating pygas to produce (1) the feed stream containing primarily $C_5$ hydrocarbons and (2) a heavy stream containing primarily $C_6+$ hydrocarbons. Embodiment 7 is the method of embodiment 6, further including separating the heavy stream in a distillation column to form a $C_{10}$ stream containing dicyclopentadiene, a $C_6$ to $C_9$ stream containing primarily $C_6$ to $C_9$ hydrocarbons, collectively, and a heavy residue stream containing $C_{10}+$ hydrocarbons. The method further includes combining the $C_{10}$ stream with the third intermediate stream to form a monomerization unit feed stream, and flowing the monomerization unit feed stream into the monomerization unit. Embodiment 8 is the method of embodiment 7, wherein the $C_{10}$ stream is a side draw of the distillation column. Embodiment 9 is the method of any of embodiments 6 to 8, wherein the method is capable of recovering at least 99% of the cyclopentadiene and at least 50% of the isoprene from the pygas. Embodiment 10 is the method of any of embodiments 6 to 9, wherein the pygas is obtained from a steam cracking unit. Embodiment 11 is the method of any of embodiments 1 to 10, wherein the processing step includes separating the first intermediate stream to form (1) a second intermediate stream containing primarily the unreacted $C_5$ hydrocarbons and (2) a third intermediate stream containing primarily dicyclopentadiene and cyclopentadiene isoprene. The method further includes subjecting, in a monomerization unit, the third intermediate stream to conditions sufficient to monomerize dicyclopentadiene in the third intermediate stream and to monomerize cyclopentadiene isoprene in the third intermediate stream to produce a fourth intermediate stream containing isoprene and cyclopentadiene. The method still further includes separating the fourth intermediate stream to produce the first product stream containing isoprene and the second product stream containing cyclopentadiene. Embodiment 12 is the method of embodiment 11, wherein the first product stream contains more than 98 wt. % isoprene and the second product stream contains more than 98 wt. % cyclopentadiene. Embodiment 13 is the method of either of embodiments 11 or 12, wherein the subjecting step further produces a residue stream containing $C_6+$ hydrocarbons. Embodiment 14 is the method of embodiment 13, wherein the dienophile does not include cyclopentadiene and the method further includes recovering the dienophile from the residue stream and flowing the recovered dienophile to the dimerization unit. Embodiment 15 is the method of any of embodiments 11 to 14, wherein the conditions in the monomerization unit include a reaction temperature of 170 to 400° C. and a reaction pressure of 1 to 5 bar. Embodiment 16 is the method of any of embodiments 11 to 15, wherein the monomerization unit is a gas phase reactor and the subjecting step is conducted in gas phase.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The invention claimed is:

1. A method of obtaining isoprene and cyclopentadiene from a $C_5$ stream, the method comprising:
    contacting, in a dimerization unit, a feed stream comprising primarily $C_5$ hydrocarbons with a dienophile under reaction conditions sufficient to dimerize cyclopentadiene and isoprene present in the feed stream to produce a first intermediate stream comprising dicyclopentadiene, cyclopentadiene isoprene, and unreacted $C_5$ hydrocarbons; and
    processing the first intermediate stream to produce a first product stream comprising primarily isoprene and a second product stream comprising primarily cyclopentadiene.

2. The method of claim 1, wherein the reaction conditions in the contacting step comprise a reaction temperature of 50 to 250° C. and reaction pressure of 3.5 to 70 bar.

3. The method of claim 1, wherein the contacting step is conducted in a dimerization unit comprising a series of reactors.

4. The method of claim 3, wherein, in the contacting step, the dienophile is added to the dimerization unit intermittently.

5. The method of claim 1, wherein the dienophile is selected from the group consisting of cyclopentadiene, anhydrides, acrylates, azocompounds, cyanocompounds, and combinations thereof.

6. The method of claim 1, further comprising prior to the contacting step, separating a pygas to produce (1) the feed stream comprising primarily $C_5$ hydrocarbons and (2) a heavy stream comprising primarily $C_{6+}$ hydrocarbons.

7. The method of claim 6, further comprising:
    separating the heavy stream in a distillation column to form a $C_{10}$ stream comprising dicyclopentadiene, a $C_6$ to $C_9$ stream comprising primarily $C_6$ to $C_9$ hydrocarbons, collectively, and a heavy residue stream comprising $C_{10}+$ hydrocarbons;
    combining the $C_{10}$ stream with the first intermediate stream to form a monomerization unit feed stream; and
    flowing the monomerization unit feed stream into a monomerization unit.

8. The method of claim 7, wherein the $C_{10}$ stream is a side draw of the distillation column.

9. The method of claim 6, wherein the method is capable of recovering at least 99% of the cyclopentadiene and at least 50% of the isoprene from the pygas.

10. The method of claim 6, wherein the pygas is obtained from a steam cracking unit.

11. The method of claim 1, wherein the processing step comprises:
    separating the first intermediate stream to form (1) a second intermediate stream comprising primarily the unreacted $C_5$ hydrocarbons and (2) a third intermediate stream comprising primarily dicyclopentadiene and cyclopentadiene isoprene;
    subjecting, in a monomerization unit, the third intermediate stream to conditions sufficient to monomerize dicyclopentadiene in the third intermediate stream and to monomerize cyclopentadiene isoprene in the third intermediate stream to produce a fourth intermediate stream comprising isoprene and cyclopentadiene; and separating the fourth intermediate stream to produce the first product stream comprising isoprene and the second product stream comprising cyclopentadiene.

12. The method of claim 11, wherein the first product stream comprises more than 98 wt. % isoprene and the second product stream comprises more than 98 wt. % cyclopentadiene.

13. The method of claim 11, wherein the subjecting step further produces a residue stream comprising $C_6+$ hydrocarbons.

14. The method of claim 13, wherein the dienophile does not include cyclopentadiene and the method further comprises:
recovering the dienophile from the residue stream; and
flowing the recovered dienophile to the dimerization unit.

15. The method of claim 11, wherein the conditions in the monomerization unit comprise a reaction temperature of 170 to 400° C. and a reaction pressure of 1 to 5 bar.

16. The method of claim 11, wherein the monomerization unit is a gas phase reactor and the subjecting step is conducted in gas phase.

17. The method of claim 12, wherein the monomerization unit is a gas phase reactor and the subjecting step is conducted in gas phase.

18. The method of claim 13, wherein the monomerization unit is a gas phase reactor and the subjecting step is conducted in gas phase.

19. The method of claim 13, wherein the monomerization unit is a gas phase reactor and the subjecting step is conducted in gas phase.

20. The method of claim 14, wherein the monomerization unit is a gas phase reactor and the subjecting step is conducted in gas phase.

* * * * *